United States Patent
Gatayama et al.

(10) Patent No.: US 9,597,051 B2
(45) Date of Patent: Mar. 21, 2017

(54) X-RAY COMPUTED TOMOGRAPHY IMAGING APPARATUS

(71) Applicant: Toshiba Medical Systems Corporation, Otawara-shi (JP)

(72) Inventors: Kazuki Gatayama, Otawara (JP); Tatsuya Watanabe, Nasushiobara (JP); Go Mukumoto, Iwata (JP); Kazumasa Arakita, Nasushiobara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 103 days.

(21) Appl. No.: 14/460,505

(22) Filed: Aug. 15, 2014

(65) Prior Publication Data

US 2015/0063535 A1    Mar. 5, 2015

(30) Foreign Application Priority Data

Aug. 30, 2013  (JP) ................. 2013-180723

(51) Int. Cl.
*A61B 6/00* (2006.01)
*A61B 6/03* (2006.01)

(52) U.S. Cl.
CPC ............ *A61B 6/5235* (2013.01); *A61B 6/032* (2013.01); *A61B 6/469* (2013.01); *A61B 6/481* (2013.01); *A61B 6/488* (2013.01); *A61B 6/545* (2013.01); *A61B 6/542* (2013.01)

(58) Field of Classification Search
CPC ....... A61B 6/032; A61B 6/5205; A61B 6/542; A61B 6/03; A61B 6/5258; A61B 6/027; A61B 6/461; A61B 6/481
See application file for complete search history.

(56) References Cited

U.S. PATENT DOCUMENTS

2012/0041304 A1*  2/2012  Seltzer ................. A61B 6/481
                                                            600/431

FOREIGN PATENT DOCUMENTS

| JP | 2002-233525 | 8/2002 |
| JP | 2009-000225 | 1/2009 |
| JP | 2011-172819 | 9/2011 |
| JP | 2013-153826 | 8/2013 |

\* cited by examiner

*Primary Examiner* — Hoon Song
(74) *Attorney, Agent, or Firm* — Oblon, McClelland, Maier & Neustadt, L.L.P.

(57) ABSTRACT

An imaging condition setting unit sets imaging conditions for a pre-contrast enhancement scan, a monitoring scan, and a post-contrast enhancement scan. A ROI setting unit sets a region of interest for the monitoring scan in a reference image generated by a reference image scan executed before the pre-contrast enhancement scan, the monitoring scan, and the post-contrast enhancement scan. The scan control unit controls an X-ray generation unit and an X-ray detection unit to sequentially execute, based on the imaging conditions, the pre-contrast enhancement scan, the monitoring scan, and the post-contrast enhancement scan.

13 Claims, 12 Drawing Sheets

Relevance of setting item of subtraction protocol
(pre-contrast enhancement scan, monitoring scan, and post-contrast enhancement scan)

| | | Pre-contrast enhancement scan | Monitoring scan | Post-contrast enhancement scan |
|---|---|---|---|---|
| Imaging conditions | | | | |
| | Tube voltage | ○ | ○ | ○ |
| | Tube current | × | × | × |
| | Rotational speed | ○ | ○ | ○ |
| | Top moving speed | ○ | × | ○ |
| | Waiting time of emission from R wave | × | × | × |
| | ... | ... | ... | ... |
| Reconstruction conditions | | | | |
| | Image reconstruction algorithm | ○ | × | ○ |
| | Reconstruction function | ○ | × | ○ |
| | ... | ... | ... | ... |

FIG. 2

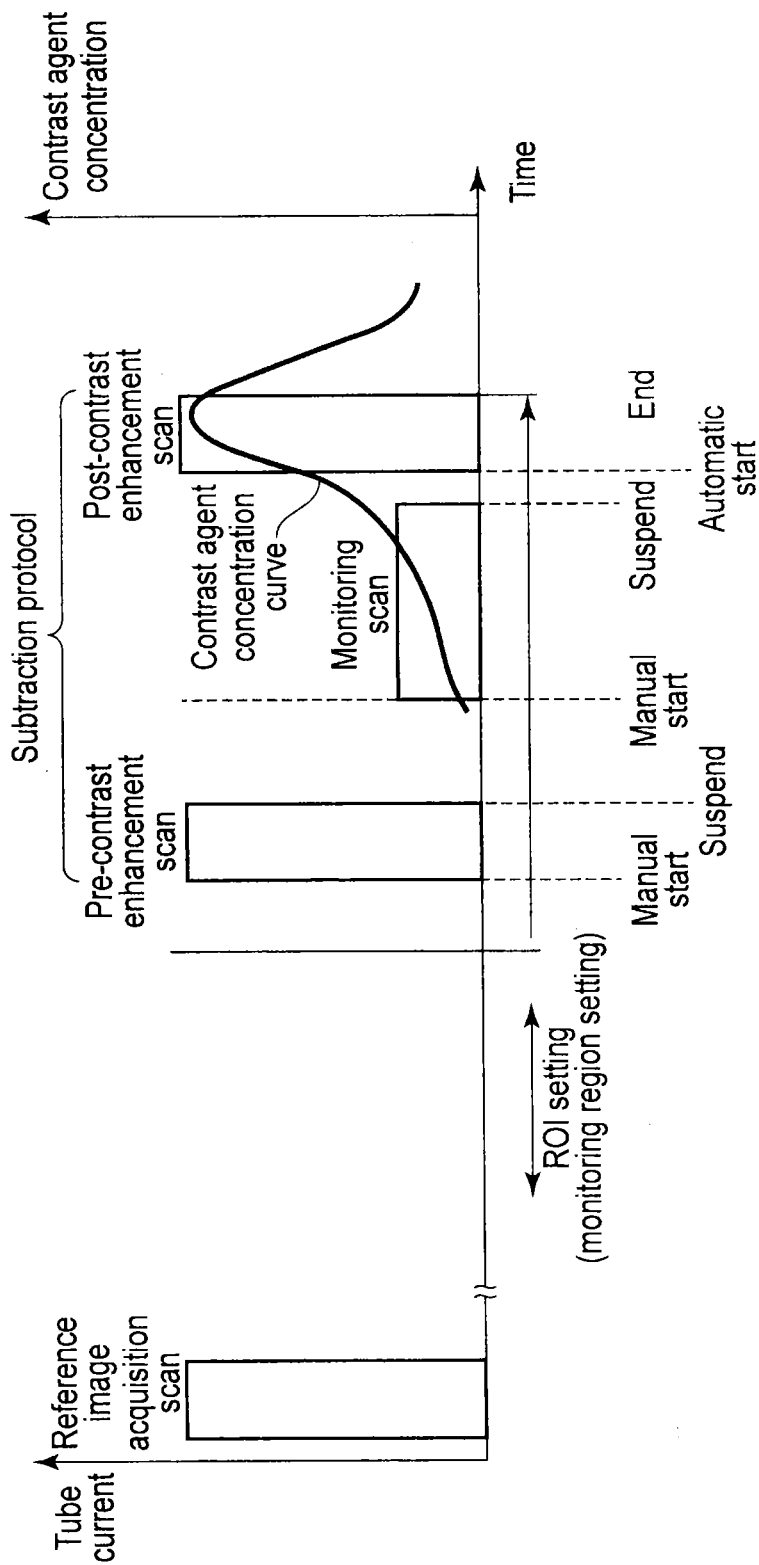
F I G. 6

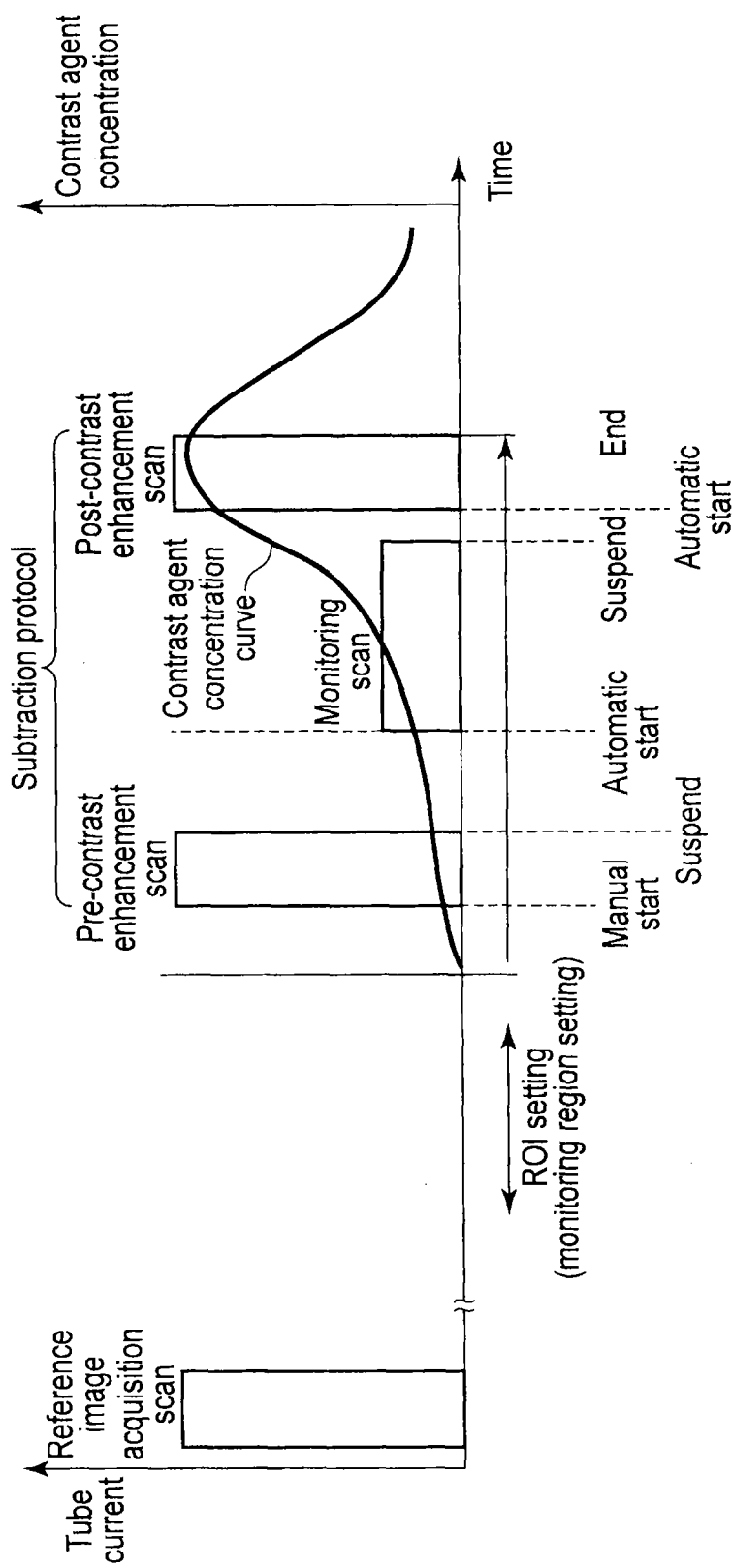
F I G. 7

F I G. 9

Subtraction conditions

| ID | Portion | Enlargement ratio | Reconstruction range | Overlapping range |
|---|---|---|---|---|
| 1 | Heart | 50mm<X<500mm | X<400mm | X<300mm |
| 2 | Head | 10mm<X<1000mm | X<300mm | X<200mm |
| 3 | Lower limbs | 80mm<X | X<2000mm | X<1500mm |

Example of determination of whether subtraction processing can be executed
(Determination based on enlargement ratio in case of heart in FIG. 9)
| Protocol | Subtraction processing | Subtraction protocol | Determination result |
|---|---|---|---|
| 1 | 50mm<X<500mm | 600mm | Subtraction processing cannot be executed |
| 2 | 50mm<X<500mm | 400mm | Subtraction processing can be executed |
F I G. 11
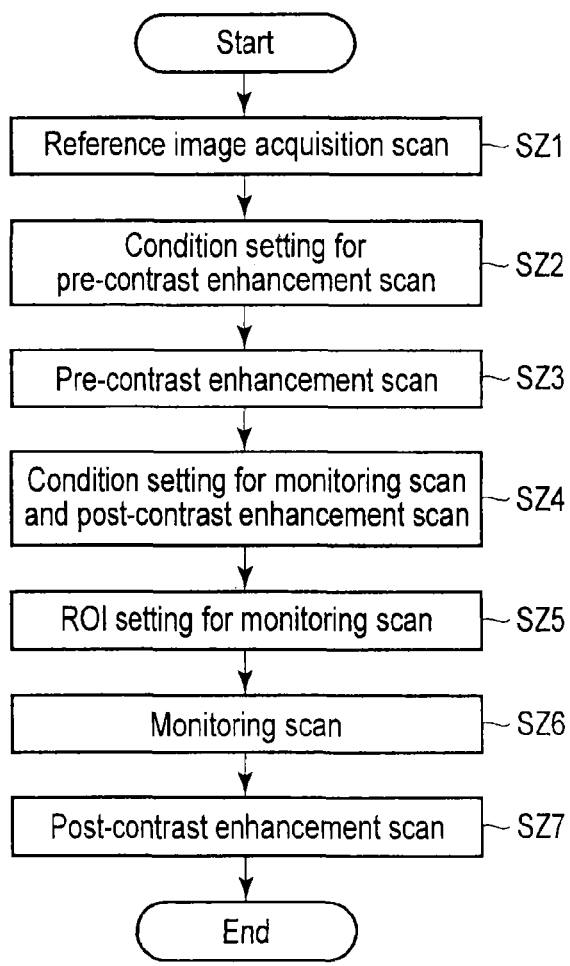
F I G. 12
Related Art

X-RAY COMPUTED TOMOGRAPHY IMAGING APPARATUS

CROSS-REFERENCE TO RELATED APPLICATIONS

This application is based upon and claims the benefit of priority from the prior Japanese Patent Application No. 2013-180723, filed Aug. 30, 2013 the entire contents of which are incorporated herein by reference.

FIELD

Embodiments described herein relate generally to an X-ray computed tomography imaging apparatus.

BACKGROUND

A monitoring scan is performed in a contrast enhancement examination by an X-ray computed tomography imaging apparatus. In the monitoring scan, the X-ray computed tomography imaging apparatus monitors in real time the degree of dyeing with a contrast agent in a CT image, and when the pixel value of the CT image reaches a specific threshold, shifts to an actual scan (to be referred to as a post-contrast enhancement scan hereinafter). The monitoring scan is a scan mode for supporting the post-contrast enhancement scan. Thus, a set of the monitoring scan and post-contrast enhancement scan is performed. Condition setting of the monitoring scan and the like are performed immediately before executing the monitoring scan.

In some cases, a scan before injecting the contrast agent (to be referred to as a pre-contrast enhancement scan hereinafter) is performed in response to a clinical request. The pre-contrast enhancement scan is performed to acquire a subtraction image between a CT image acquired by the pre-contrast enhancement scan and a CT image acquired by the post-contrast enhancement scan.

FIG. 12 is a flowchart showing the typical sequence of a contrast enhancement examination according to a related art. FIG. 13 is a graph schematically showing the flow of the contrast enhancement examination according to the related art. As shown in FIGS. 12 and 13, a reference image acquisition scan is performed first (step SZ1). After the end of step SZ1, condition setting for the pre-contrast enhancement scan is performed (step SZ2). More specifically, in step SZ2, imaging conditions, reconstruction conditions, and the like are set. The pre-contrast enhancement scan is performed in accordance with the conditions set in step SZ2 (step SZ3). After performing step SZ3, condition setting for the monitoring scan and post-contrast enhancement scan is performed (step SZ4). By using a reference image acquired in step SZ1, an ROI (Region Of Interest) for the monitoring scan is set (step SZ5). After performing steps SZ4 and SZ5, a contrast agent is injected into a subject, and the monitoring scan is performed (step SZ6). If a pixel value in the ROI of the CT image acquired by the monitoring scan reaches a threshold, the post-contrast enhancement scan is performed (step SZ7). Then, the contrast enhancement examination ends.

ROI setting for the monitoring scan cannot be performed before the start of the pre-contrast enhancement scan. That is, the ROI setting has to be performed between the end of the pre-contrast enhancement scan and the start of the monitoring scan. Time is therefore taken for a shift from the pre-contrast enhancement scan to the monitoring scan. The conditions of the pre-contrast enhancement scan, monitoring scan, and post-contrast enhancement scan are set individually. For this reason, an error of the condition setting readily occurs. Also, the number of condition setting operations is large, and the working efficiency is poor.

BRIEF DESCRIPTION OF THE DRAWINGS

FIG. 2 is a table showing an example of the relevance of a setting item between scan types regarding a subtraction protocol that is stored in a relevance storage unit in FIG. 1;

FIG. 6 is a graph schematically showing a typical scan sequence in a contrast enhancement examination according to Example 1;

FIG. 7 is a graph schematically showing a typical scan sequence in a contrast enhancement examination according to Example 2;

FIG. 9 is a table showing an example of a subtraction condition table stored in a subtraction condition storage unit in FIG. 8;

FIG. 11 is a table for explaining determination processing to be executed by a determination unit in step SC4 of FIG. 10;

FIG. 12 is a flowchart showing the typical sequence of a contrast enhancement examination according to a related art.

DETAILED DESCRIPTION

An X-ray computed tomography imaging apparatus according to an embodiment comprises an X-ray generation unit, X-ray detection unit, imaging condition setting unit, region-of-interest setting unit, and scan control unit. The X-ray generation unit generates X-rays. The X-ray detection unit detects X-rays which have been generated from the X-ray generation unit and have passed through a subject. The imaging condition setting unit sets imaging conditions for a pre-contrast enhancement scan, a monitoring scan, and a post-contrast enhancement scan. The region-of-interest setting unit sets a region of interest for the monitoring scan in a reference image generated by a reference image scan executed before the pre-contrast enhancement scan, the monitoring scan, and the post-contrast enhancement scan. The scan control unit controls the X-ray generation unit and the X-ray detection unit to sequentially execute, based on the imaging conditions, the pre-contrast enhancement scan, the monitoring scan, and the post-contrast enhancement scan.

The X-ray computed tomography imaging apparatus according to the embodiment will now be described with reference to the accompanying drawings.

Figure 1:
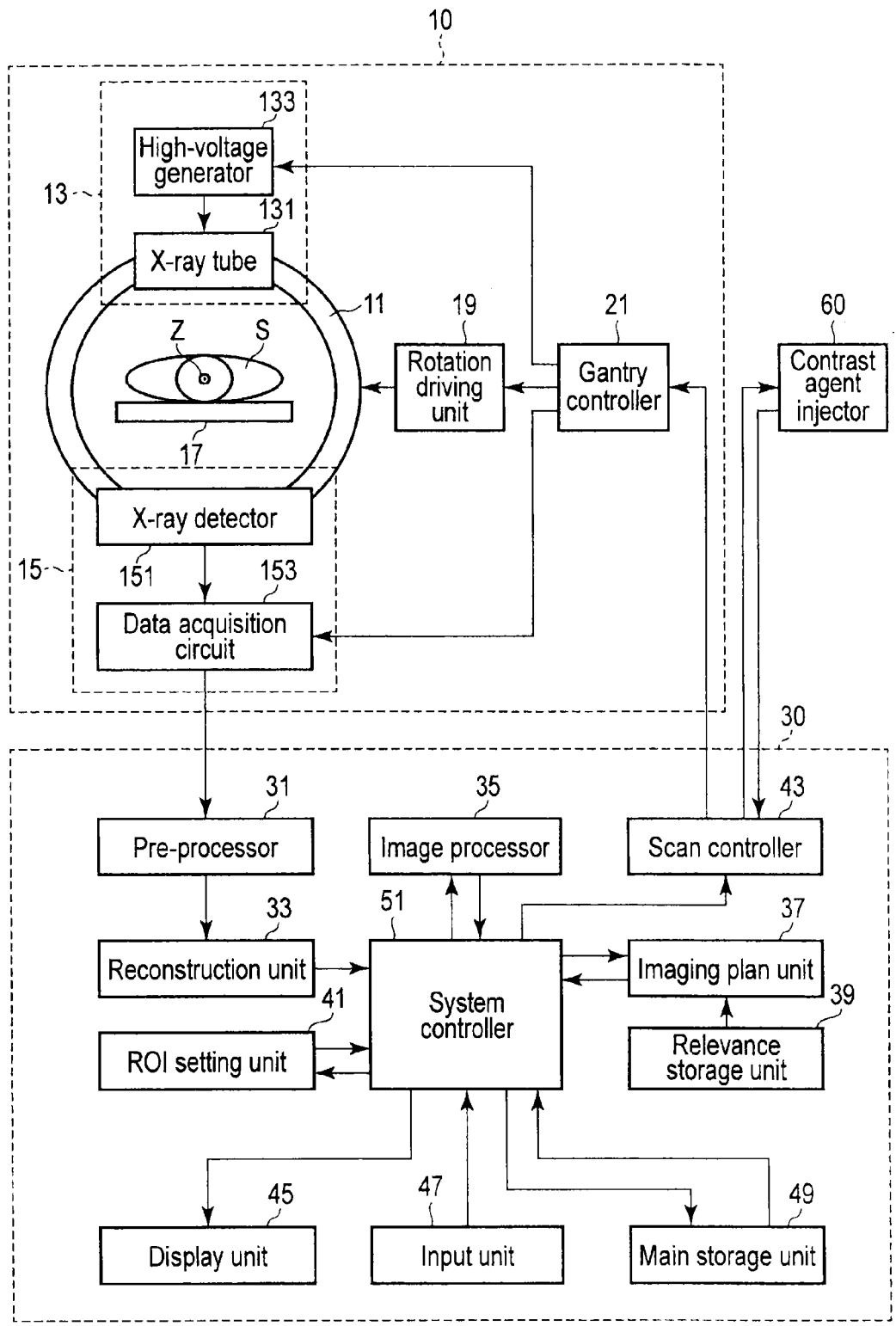
FIG. 1 is a view showing the arrangement of an X-ray computed tomography imaging apparatus according to an embodiment.

FIG. 1 is a view showing the arrangement of the X-ray computed tomography imaging apparatus according to the embodiment. As shown in FIG. 1, the X-ray computed tomography imaging apparatus according to the embodiment includes a gantry 10, console 30, and contrast agent injector 60. The gantry 10 supports a rotating frame 11 having a cylindrical shape so that the rotating frame 11 can rotate about a rotation axis Z. An X-ray generation unit 13 and X-ray detection unit 15 are attached to the rotating frame 11 so that they face each other via the rotation axis Z. An FOV (Field Of View) is set in the opening of the rotating frame 11. A top 17 is inserted in the opening of the rotating frame 11. A subject S is placed on the top 17. The top 17 is positioned so that the imaging portion of the subject S on the top 17 falls in the FOV. The rotating frame 11 rotates at a predetermined angular velocity about the rotation axis Z upon receiving power from a rotation driving unit 19. The rotation driving unit 19 generates power for rotating the rotating frame 11 in accordance with a control signal from a gantry controller 21.

The X-ray generation unit 13 generates X-rays in accordance with a control signal from the gantry controller 21. More specifically, the X-ray generation unit 13 includes an X-ray tube 131 and high-voltage generator 133. The X-ray tube 131 generates X-rays upon receiving the application of a high voltage from the high-voltage generator 133, and the supply of a filament current. The high-voltage generator 133 applies, to the X-ray tube 131, a high voltage complying with a control signal from the gantry controller 21, and supplies, to the X-ray tube 131, a filament current complying with a control signal from the gantry controller 21.

The X-ray detection unit 15 detects X-rays which have been generated from the X-ray generation unit 13 and have passed through the subject S, and generates digital data corresponding to the intensity of the detected X-rays. More specifically, the X-ray detection unit 15 includes an X-ray detector 151 and data acquisition circuit 153.

The X-ray detector 151 detects X-rays generated from the X-ray tube 131. The X-ray detector 151 includes a plurality of X-ray detection elements arrayed two-dimensionally. Each X-ray detection element detects X-rays from the X-ray tube 131, and generates an electrical signal corresponding to the energy of the detected X-rays.

The data acquisition circuit 153 acquires electrical signals from the respective X-ray detection elements for each view, and converts the acquired electrical signals into digital data. The converted digital data is called raw data. The raw data is supplied to the console 30.

The gantry controller 21 supervises the control of various devices mounted in the gantry 10 in accordance with an instruction from a scan controller 43 in the console 30. For example, the gantry controller 21 controls the X-ray generation unit 13, X-ray detection unit 15, and rotation driving unit 19 to execute a CT scan targeting the subject S in which a contrast agent has been injected according to the embodiment. The rotation driving unit 19 rotates at a predetermined angular velocity under the control of the gantry controller 21. Under the control of the gantry controller 21, the high-voltage generator 133 of the X-ray generation unit 13 applies, to the X-ray tube 131, a tube voltage having a tube voltage value set in advance. Under the control of the gantry controller 21, the data acquisition circuit 153 of the X-ray detection unit 15 acquires raw data for each view in synchronism with the X-ray emission timing.

The contrast agent injector 60 is a device for injecting a contrast agent into the subject S. The contrast agent injector 60 may inject the contrast agent into the subject S by a manual operation by the user, or inject it in synchronism with reception of an injection start signal from the scan controller 43 in the console 30. The contrast agent injector 60 may transmit an emission start signal to the scan controller 43 in synchronism with injection of the contrast agent by a manual operation by the user. Upon receiving the emission start signal, the scan controller 43 transmits an emission start signal to the gantry controller 21 in order to start emission of X-rays.

The console 30 includes a pre-processor 31, a reconstruction unit 33, an image processor 35, an imaging plan unit 37, a relevance storage unit 39, an ROI setting unit 41, the scan controller 43, a display unit 45, an input unit 47, a main storage unit 49, and a system controller 51.

The pre-processor 31 performs pre-processing such as logarithmic transformation on raw data from the gantry 10. Raw data after pre-processing is called projection data. The pre-processing includes various correction processes such as logarithmic transformation, X-ray intensity correction, and offset correction.

Based on projection data, the reconstruction unit 33 generates a CT image expressing the spatial distribution of CT values regarding the subject S. More specifically, the reconstruction unit 33 performs image reconstruction processing on a CT image in accordance with reconstruction conditions set by the imaging plan unit 37. The image reconstruction algorithm suffices to be an existing image reconstruction algorithm such as an analytic image reconstruction method (e.g., FBP (Filtered Back Projection) or CBP (Convolution Back Projection)), or a statistical image reconstruction method (e.g., ML-EM (Maximum Likelihood Expectation Maximization) or OS-EM (Ordered Subset Expectation Maximization)).

The image processor 35 performs various image processes on a CT image. For example, the image processor 35 performs subtraction processing on two CT images to generate a subtraction image.

The imaging plan unit 37 executes an imaging plan in accordance with an instruction from the user via the input unit 47. In the imaging plan, an examination protocol is built. The examination protocol is constituted by a plurality of scan types to be executed at once as one unit. The scan types according to the embodiment can be any existing scan types such as a reference image acquisition scan, pre-contrast enhancement scan, monitoring scan, and post-contrast enhancement scan. The scan types may include a scan in an arbitrary contrast agent inflow phase in a contrast enhancement examination. As the scan in the contrast agent inflow phase, for example, an early inflow phase scan, peak inflow phase scan, and late inflow phase scan are known. A combination of scan types constituting an examination protocol to be executed may be set in advance or set by the user via the input unit 47. After determining scan types to be included in the examination protocol, imaging conditions and reconstruction conditions for the examination protocol are set. More specifically, by using relevance regarding the examination protocol that is stored in the relevance storage unit 39, the imaging plan unit 37 sets, in synchronism with an instruction from the user via the input unit 47, the item values of a plurality of setting items included in the imaging conditions and reconstruction conditions of the examination protocol to be set.

For each of a plurality of examination protocols, the relevance storage unit 39 stores the relevance, between scan types, of a plurality of setting items included in the imaging conditions and reconstruction conditions of each examination protocol. The relevance is defined by, e.g., an LUT (Look Up Table) or database. The relevance is assumed to be defined by an LUT, and this LUT will be called a relevance table. The relevance table defines the relevance of a setting item between scan types included in a given examination protocol. The relevance table is set for each examination protocol. The user can arbitrarily set/change the contents of the relevance table via the input unit 47.

FIG. 2 is a table showing an example of the relevance of a setting item between scan types regarding a subtraction protocol. The subtraction protocol is constituted by the pre-contrast enhancement scan, monitoring scan, and post-contrast enhancement scan, which will be described later. As shown in FIG. 2, the setting items are classified into setting items for the imaging conditions, and setting items for the reconstruction conditions. The setting items for the imaging conditions are, e.g., a tube voltage, a tube current, the rotational speed of the rotating frame 11, and the top moving speed. The setting items for the reconstruction conditions are, e.g., an image reconstruction algorithm and reconstruction function. In FIG. 2, "○" represents that there is relevance, and "x" represents that there is no relevance. For example, as shown in FIG. 2, the setting item "tube voltage" has relevance between the pre-contrast enhancement scan, the monitoring scan, and the post-contrast enhancement scan. The setting item "tube current" does not have relevance between the pre-contrast enhancement scan, the monitoring scan, and the post-contrast enhancement scan. The setting item "reconstruction function" has relevance between the pre-contrast enhancement scan and the post-contrast enhancement scan, and does not have relevance between the pre-contrast enhancement scan and the monitoring scan and between the post-contrast enhancement scan and the monitoring scan.

As for a setting item having relevance, the imaging plan unit 37 synchronously sets the setting item between a plurality of scan types. As for a setting item having no relevance, the imaging plan unit 37 individually sets the setting item between a plurality of scan types.

The ROI setting unit 41 sets an ROI (Region Of Interest) in a CT image in accordance with an instruction from the user via the input unit 47. The ROI is used in the monitoring scan.

The scan controller 43 controls the gantry controller 21 and contrast agent injector 60 in order to execute a CT scan. For example, the scan controller 43 controls the gantry controller 21 in accordance with the imaging conditions set by the imaging plan unit 37. The scan controller 43 supplies an emission start signal to the gantry controller 21 in response to input of an emission start instruction from the user via the input unit 47. Also, the scan controller 43 supplies an emission stop signal to the gantry controller 21 in response to input of an emission stop instruction from the user via the input unit 47. Upon receiving the supply of the emission start signal, the gantry controller 21 controls the high-voltage generator 133 to start emission of X-rays from the X-ray tube 131. Upon receiving the supply of the emission stop signal, the gantry controller 21 controls the high-voltage generator 133 to stop the emission of X-rays from the X-ray tube 131. The scan controller 43 supplies an injection start signal to the contrast agent injector 60 in response to input of an injection start instruction from the user via the input unit 47. Further, the scan controller 43 supplies an injection stop signal to the contrast agent injector 60 in response to input of an injection stop instruction from the user via the input unit 47. Upon receiving the supply of the injection start signal, the gantry controller 21 controls the contrast agent injector 60 to start injection of a contrast agent. Upon receiving the supply of the injection stop signal, the gantry controller 21 controls the contrast agent injector 60 to stop the injection of the contrast agent.

The display unit 45 displays, on a display device, a CT image, imaging plan setting screen, and the like. As the display device, for example, a CRT display, liquid crystal display, organic EL display, or plasma display is appropriately available.

The input unit 47 accepts various instructions and information inputs from the user via an input device. For example, the user inputs, via the input device, an instruction for setting imaging conditions and reconstruction conditions. The user may input, via the input device, an emission start instruction, emission stop instruction, injection start instruction, and injection stop instruction. As the input device, for example, a keyboard, mouse, or various switches are available.

The main storage unit 49 is a storage device which stores various kinds of information. For example, the main storage unit 49 stores projection data and CT images. Also, the main storage unit 49 stores an imaging plan program and examination protocol execution program according to the embodiment.

The system controller 51 functions as the center of the X-ray computed tomography imaging apparatus. The system controller 51 reads out the imaging plan program according to the embodiment from the main storage unit 49, and controls various building components in accordance with the imaging plan program. As a result, imaging plan processing according to the embodiment is performed. In addition, the system controller 51 reads out the examination protocol execution program according to the embodiment from the main storage unit 49, and controls various building components in accordance with the examination protocol execution program. Hence, examination protocol execution processing according to the embodiment is executed.

Next, an example of the operation of the X-ray computed tomography imaging apparatus according to the embodiment will be described. First, imaging plan processing according to the embodiment will be explained.

Figure 3:
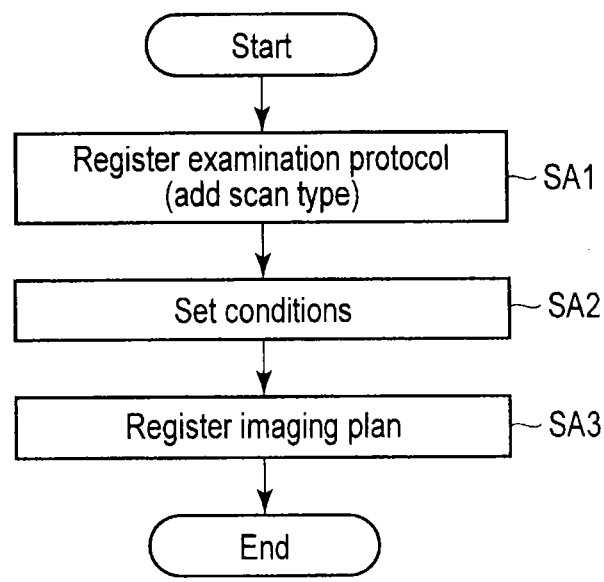
FIG. 3 is a flowchart showing the typical sequence of imaging plan processing to be performed by an imaging plan unit in FIG. 1.

FIG. 3 is a flowchart showing the typical sequence of imaging plan processing to be performed by the imaging plan unit 37 according to the embodiment. The imaging plan according to the embodiment is performed for an examination protocol including a plurality of scan types. Condition setting needs to be performed for all scan types constituting the examination protocol. In the imaging plan according to the embodiment, condition setting is performed at once for all scan types constituting the examination protocol.

As shown in FIG. 3, the system controller 51 controls the imaging plan unit 37 to start imaging plan processing in response to input of an imaging plan processing start instruction from the user via the input unit 47. First, the imaging plan unit 37 builds an examination protocol (step SA1). In step SA1, the imaging plan unit 37 selects, from a plurality of scan types set in advance, scan types to be included in the examination protocol of an examination target. For example, in step SA1, the display unit 45 displays a list of a plurality of scan types. The user selects, from the displayed list via the input unit 47, a plurality of scan types to be included in the examination protocol. The user can select a plurality of arbitrary necessary scan types in accordance with examination contents. For example, scan types are arbitrarily selected from existing scan types such as the reference image acquisition scan, pre-contrast enhancement scan, monitoring scan, and post-contrast enhancement scan. The imaging plan unit 37 registers, as the examination protocol of the examination target, a set of scan types selected via the input unit 47.

After performing step SA1, the imaging plan unit 37 performs condition setting processing (step SA2). In step SA2, in synchronism with an instruction from the user via the input unit 47, the imaging plan unit 37 sets the item values of a plurality of setting items included in the imaging conditions and reconstruction conditions of the examination protocol in accordance with relevance regarding the examination protocol that is stored in the relevance storage unit 39.

Figure 4:
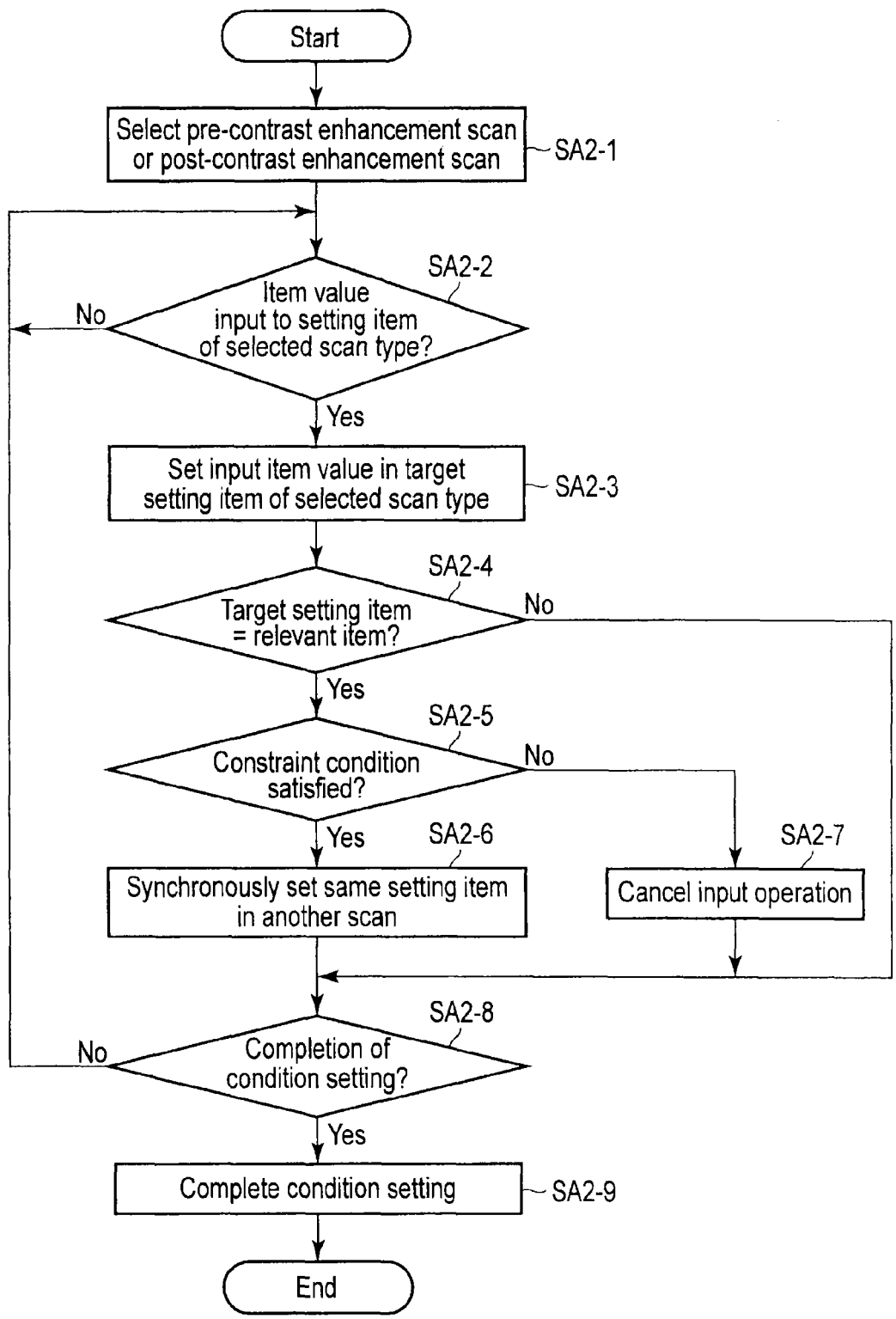
FIG. 4 is a flowchart showing the typical sequence of condition setting processing to be performed by the imaging plan unit in step SA2 of FIG. 3.

FIG. 4 is a flowchart showing the typical sequence of condition setting processing to be performed by the imaging plan unit 37 in step SA2. In the description of FIG. 4, the subtraction protocol is assumed to be registered as the examination protocol. As described above, the subtraction protocol is constituted by the pre-contrast enhancement scan, monitoring scan, and post-contrast enhancement scan.

First, in accordance with an instruction from the user via the input unit 47, the imaging plan unit 37 selects a scan type serving as the input target of setting items (step SA2-1). For the subtraction protocol, a scan type is selected from the pre-contrast enhancement scan, monitoring scan, and post-contrast enhancement scan. Note that the scan type selected in step SA2-1 will be called a selected scan type.

After performing step SA2-1, the imaging plan unit 37 waits for input of an item value to a setting item in the selected scan type by the user via the input unit 47 (step SA2-2). For example, if the pre-contrast enhancement scan is selected in step SA2-1, an item value "80 kV" of the setting item "tube voltage" in the pre-contrast enhancement scan is input.

If an item value has been input (step SA2-2: YES), the imaging plan unit 37 sets the item value input in step SA2-2 in the target setting item of the selected scan type (step SA2-3). For example, if the pre-contrast enhancement scan is selected in step SA2-1, and the item value "80 kV" of the setting item "tube voltage" is input in step SA2-2, the "tube voltage" in the pre-contrast enhancement scan is set to "80 kV" in step SA2-3.

In step SA2-3, the imaging plan unit 37 reads out a relevance table from the relevance storage unit 39, and determines whether the setting item whose item value has been input in step SA2-2 is a relevant item (step SA2-4). In step SA2-4, by looking up the relevance table, the imaging plan unit 37 determines whether the setting item has relevance between the pre-contrast enhancement scan and the post-contrast enhancement scan. An item having relevance is determined to be a relevant item. An item having no relevance is determined not to be a relevant item. For example, the setting item "tube voltage" has relevance between the pre-contrast enhancement scan and the post-contrast enhancement scan, as shown in FIG. 2. Hence, the setting item "tube voltage" is determined to be a relevant item. Also, a setting item "waiting time of emission from an R wave" does not have relevance between the pre-contrast enhancement scan, the monitoring scan, and the post-contrast enhancement scan, as shown in FIG. 2. The setting item "waiting time of emission from an R wave" is therefore determined not to be a relevant item.

If the imaging plan unit 37 determines in step SA2-4 that the setting item is a relevant item (step SA2-4: YES), it determines whether the setting item satisfies a constraint condition (step SA2-5). The constraint condition is a condition for restricting input of an item value. As the constraint condition, for example, the allowable range of an item value is set for each setting item. The imaging plan unit 37 determines whether the item value input in step SA2-2 falls within the allowable range. If the input item value falls within the allowable range, the imaging plan unit 37 determines that the constraint condition is satisfied. If the input item value falls outside the allowable range, the imaging plan unit 37 determines that the constraint condition is not satisfied. As another constraint condition, input of a new item value is restricted for a setting item whose item value has already been input by synchronous setting in step SA2-6. In this case, the imaging plan unit 37 specifies whether the setting item whose item value has been input in step SA2-2 is an item already input by synchronous setting in step SA2-6. If this setting item is an input item, the imaging plan unit 37 determines that the constraint condition is satisfied. If this setting item is not an input item, the imaging plan unit 37 determines that the constraint condition is not satisfied.

If the imaging plan unit 37 determines in step SA2-5 that the constraint condition is satisfied (step SA2-5: YES), it synchronously sets the same setting item of an unselected scan type (step SA2-6). More specifically, the imaging plan unit 37 sets the item value input in step SA2-2 in the same setting item for all unselected scan types each having relevance with the selected scan type. For example, if the pre-contrast enhancement scan is selected in step SA2-1 and the item value "80 kV" of the setting item "tube voltage" is input in step SA2-2, the same item value "80 kV" is set in the setting item "tube voltage" in the post-contrast enhancement scan and monitoring scan. Also, if the pre-contrast enhancement scan is selected in step SA2-1 and an item value "3" of the setting item "reconstruction function" is input in step SA2-2, the same item value "3" is set in the same setting item "reconstruction function" in the post-contrast enhancement scan, and the same setting item "reconstruction function" in the monitoring scan maintains an initial value without setting "3".

If the imaging plan unit 37 determines in step SA2-5 that the constraint condition is not satisfied (step SA2-5: NO), it cancels the input operation in step SA2-2 (step SA2-7). That is, the item value set in step SA2-3 is canceled, and a value before the setting or an initial value is set again.

If it is determined in step SA2-4 that the setting item is not a relevant item (step SA2-4: NO), step SA2-6 is performed, or step SA2-7 is performed, the imaging plan unit 37 determines whether an instruction to end the condition setting processing has been input via the input unit 47 (step SA2-8). If the instruction to end the condition setting processing has not been input (step SA2-8: NO), the imaging plan unit 37 returns again to step SA2-2, and waits for input of an item value to a setting item in the selected scan type by the user via the input unit 47.

In this manner, if the condition setting is performed for all setting items, and the instruction to end the condition setting processing has been input via the input unit 47 (step SA2-8: YES), the imaging plan unit 37 ends the condition setting processing (step SA2-9).

The condition setting processing is repetitively executed for each scan type until item values are set in all the setting items of all scan types included in the examination protocol of the examination target. If item values are set in all the setting items of all scan types included in the examination protocol of the examination target, the imaging plan processing (more specifically, condition setting processing) on the examination protocol of the examination target is completed.

As shown in FIG. 3, after performing step SA2, the imaging plan unit 37 registers the imaging plan of the examination protocol of the examination target (step SA3). The main storage unit 49 stores the registered imaging plan.

As described above, the imaging plan processing according to the embodiment makes it possible to perform condition setting at once for the pre-contrast enhancement scan, monitoring scan, and post-contrast enhancement scan. Therefore, the condition setting of an efficient subtraction protocol can be performed efficiently. The condition setting can be performed accurately and simply by synchronously performing the condition setting for a relevant item, and imposing a constraint.

Next, an example of the operation of the examination protocol according to the embodiment will be explained. Assume that the examination protocol according to the embodiment is a clinically beneficial subtraction protocol in a contrast enhancement examination.

Figure 5:
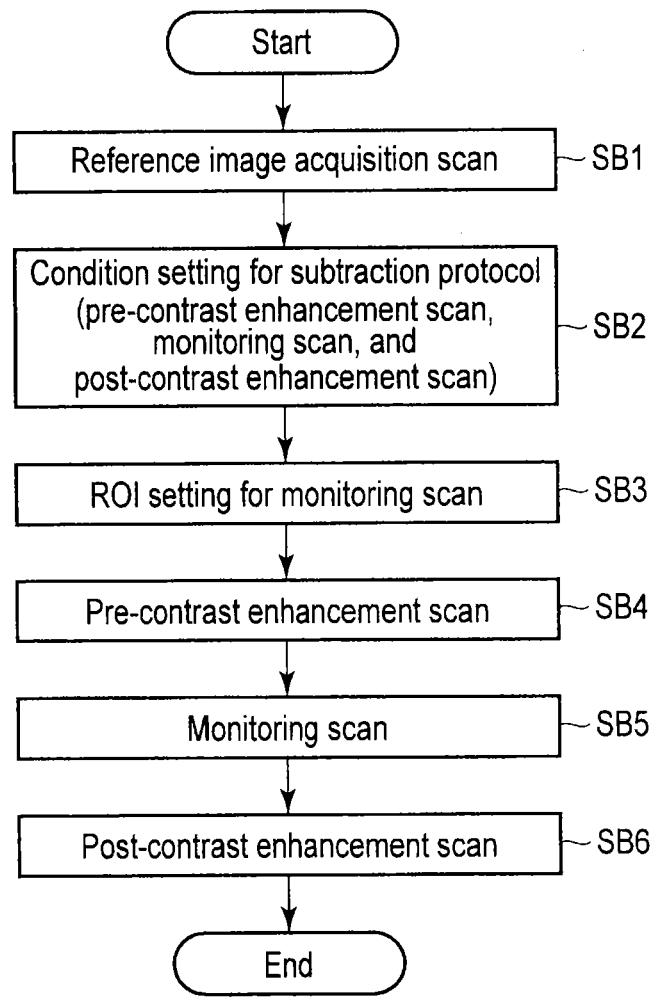
FIG. 5 is a flowchart showing the typical sequence of a contrast enhancement examination to be performed under the control of a system controller in FIG. 1 according to the embodiment.

FIG. 5 is a flowchart showing the typical sequence of a contrast enhancement examination to be performed under the control of the system controller 51 according to the embodiment. As shown in FIG. 5, the reference image acquisition scan is performed first (step SB1). The reference image acquisition scan is a scan for acquiring a reference image to be used to set an ROI for the monitoring scan. The system controller 51 reads out, from the main storage unit 49, preset imaging conditions for the reference image scan, and supplies them to the scan controller 43. In addition, the system controller 51 reads out, from the main storage unit 49, preset reconstruction conditions for the reference image scan, and supplies them to the reconstruction unit 33. The scan controller 43 transmits the imaging conditions to the gantry controller 21. Further, the scan controller 43 transmits an emission start signal to the gantry controller 21 in response to input of an emission start instruction via the input unit 47. In response to supply of an emission start signal, the gantry controller 21 controls the X-ray generation unit 13 and X-ray detection unit 15 in accordance with the imaging conditions to execute the reference image acquisition scan. In the reference image acquisition scan, based on raw data acquired by the data acquisition circuit 153, the reconstruction unit 33 generates a CT image (to be referred to as a reference image hereinafter) in accordance with reconstruction conditions for the reference image acquisition scan. The main storage unit 49 stores the reference image.

After performing step SB1, the imaging plan of the subtraction protocol is determined (step SB2). In step SB2, the imaging plan unit 37 determines the imaging plan of the subtraction protocol by the above-described imaging plan processing. As described above, the imaging conditions and reconstruction conditions of the pre-contrast enhancement scan, monitoring scan, and post-contrast enhancement scan can be set at once by the imaging plan processing according to the embodiment. With the synchronous setting function, the item value of a relevant item can be synchronously set between a plurality of scan types. The item value of the relevant item can reliably become the same between a plurality of scan types. The main storage unit 49 stores the determined imaging plan of the subtraction protocol.

After performing step SB2, the ROI setting unit 41 performs ROI setting processing (step SB3). In ROI setting processing, the ROI setting unit 41 sets an ROI for the monitoring scan in the reference image in accordance with an instruction from the user via the input unit 47. Pixel values in the set ROI are monitored in the monitoring scan. The ROI for the monitoring scan will be called a monitoring region.

After performing step SB3, the scan controller 43 controls the X-ray generation unit 13 and X-ray detection unit 15 to sequentially execute the pre-contrast enhancement scan, monitoring scan, and post-contrast enhancement scan as a single examination protocol.

More specifically, the pre-contrast enhancement scan is performed first (step SB4). The pre-contrast enhancement scan is a scan targeting the imaging portion of a subject before the contrast of the imaging portion is enhanced with a contrast agent. The system controller 51 reads out, from the main storage unit 49, imaging conditions for the pre-contrast enhancement scan, imaging conditions for the monitoring scan, and imaging conditions for the post-contrast enhancement scan which have been set in step SB2, and supplies them to the scan controller 43. In addition, the system controller 51 reads out, from the main storage unit 49, reconstruction conditions for the pre-contrast enhancement scan, reconstruction conditions for the monitoring scan, and reconstruction conditions for the post-contrast enhancement scan, and supplies them to the reconstruction unit 33. The scan controller 43 transmits the imaging conditions to the gantry controller 21. The scan controller 43 transmits an emission start signal to the gantry controller 21 in response to input of an emission start instruction via the input unit 47. In response to the supply of the emission start signal, the gantry controller 21 controls the X-ray generation unit 13 and X-ray detection unit 15 to execute the pre-contrast enhancement scan in accordance with the imaging conditions for the pre-contrast enhancement scan. In the pre-contrast enhancement scan, based on raw data acquired by the data acquisition circuit 153, the reconstruction unit 33 generates a CT image (to be referred to as a pre-contrast enhancement CT image hereinafter) in accordance with the reconstruction conditions for the pre-contrast enhancement scan. The main storage unit 49 stores the pre-contrast enhancement CT image.

After performing step SB4, the scan controller 43 executes the monitoring scan (step SB5). The monitoring scan is a scan to be performed to detect the timing when the contrast of the imaging portion of the subject S is appropriately enhanced with the contrast agent, in order to perform the post-contrast enhancement scan at this timing. The contrast agent is injected into the subject S before executing the monitoring scan. More specifically, the scan controller 43 transmits the imaging conditions for the monitoring scan to the gantry controller 21. The scan controller 43 transmits an emission start signal to the gantry controller 21 in response to input of an emission start instruction via the input unit 47. The gantry controller 21 controls the X-ray generation unit 13 and X-ray detection unit 15 to execute the monitoring scan in accordance with the imaging conditions for the monitoring scan. Typically in the monitoring scan, X-rays are continuously emitted at a lower dose than in the pre-contrast enhancement scan and post-contrast enhancement scan. In the monitoring scan, the reconstruction unit 33 repetitively generates CT images (to be referred to as monitoring images hereinafter) based on projection data from the data acquisition circuit 153 in accordance with the reconstruction conditions for the monitoring scan.

In the monitoring scan, the scan controller 43 calculates, for each monitoring image, the statistical value of the pixel values of a plurality of pixels in the monitoring region set in the monitoring image in step SB3, and compares the calculated statistical value with a threshold. The statistical value is set as, e.g., the average value, maximum value, minimum value, or intermediate value of the pixel values of a plurality of pixels. The threshold suffices to be set as a typical pixel value of a pixel corresponding to a blood vessel portion whose contrast has been sufficiently enhanced with the contrast agent. The threshold can be arbitrarily set in accordance with an instruction from the user via the input unit 47. If the scan controller 43 determines that the statistical value is smaller than the threshold, it controls the X-ray generation unit 13 and X-ray detection unit 15 to keep executing the monitoring scan. If the scan controller 43 determines that the statistical value is larger than the threshold, it controls the X-ray generation unit 13 and X-ray detection unit 15 to stop the monitoring scan.

After performing step SB5, the scan controller 43 executes the post-contrast enhancement scan (step SB6). The post-contrast enhancement scan is a scan which targets the imaging portion of the subject, and is performed while the contrast of the imaging portion is appropriately enhanced with the contrast agent. More specifically, the scan controller 43 controls the X-ray generation unit 13 and X-ray detection unit 15 to execute the post-contrast enhancement scan in accordance with the imaging conditions for the post-contrast enhancement scan. By the post-contrast enhancement scan, a CT image (to be referred to as a post-contrast enhancement CT image hereinafter) is generated. In the post-contrast enhancement scan, based on raw data acquired by the data acquisition circuit 153, the reconstruction unit 33 generates a CT image (to be referred to as a post-contrast enhancement CT image hereinafter) in accordance with the reconstruction conditions for the post-contrast enhancement scan.

The monitoring scan may be started manually or automatically. A case in which the monitoring scan is started manually will be explained as Example 1. A case in which the monitoring scan is started automatically will be explained as Example 2.

Example 1

FIG. 6 is a graph schematically a typical scan sequence in a contrast enhancement examination according to Example 1. In FIG. 6, the left ordinate defines the tube voltage, the right ordinate defines the contrast agent concentration, and the abscissa defines the time. As described above, an ROI (monitoring region) for the monitoring scan is set at the preceding stage of the pre-contrast enhancement scan. The pre-contrast enhancement scan, monitoring scan, and post-contrast enhancement scan are executed sequentially as a single examination protocol (subtraction protocol). The scan controller 43 starts the pre-contrast enhancement scan in accordance with a manual instruction from the user via the input unit 47. After X-ray emission is performed a predetermined number of times for the pre-contrast enhancement scan, the scan controller 43 automatically stops the pre-contrast enhancement scan. After the stop of the pre-contrast enhancement scan, the user injects a contrast agent into the subject S. Then, the scan controller 43 starts the monitoring scan in accordance with a manual instruction from the user via the input unit 47. Note that the contrast agent injector 60 may automatically inject the contrast agent. That is, after the stop of the pre-contrast enhancement scan, the scan controller 43 transmits an injection start signal to the contrast agent injector 60. Upon receiving the injection start signal, the contrast agent injector 60 automatically injects the contrast agent into the subject S. In synchronism with the transmission of the injection start signal to the contrast agent injector 60, the scan controller 43 transmits an emission start signal to the gantry controller 21. Alternatively, the contrast agent injector 60 may transmit an emission start signal to the scan controller 43 in synchronism with an injection operation to the contrast agent injector 60 by the user, and the scan controller 43 may transmit an emission start signal to the gantry controller 21 in response to the reception of the emission start signal. This can synchronize the injection of the contrast agent with X-ray emission in the monitoring scan. When the monitoring scan is performed and the contrast agent concentration (i.e., a statistical value based on the pixel values of a plurality of pixels in the monitoring region) reaches a threshold, the monitoring scan is stopped, and the post-contrast enhancement scan automatically starts upon the lapse of a predetermined period. After X-ray emission is performed a predetermined number of times for the post-contrast enhancement scan, the scan controller 43 automatically stops the post-contrast enhancement scan.

As described above, according to Example 1, the pre-contrast enhancement scan is manually shifted to the monitoring scan. The start timing of the subtraction protocol and the like can be reliably determined, compared to Example 2 to be described below.

Example 2

FIG. 7 is a graph schematically showing a typical scan sequence in a contrast enhancement examination according to Example 2. As in FIG. 6, an ROI (monitoring region) for the monitoring scan is set at the preceding stage of the pre-contrast enhancement scan. The pre-contrast enhancement scan, monitoring scan, and post-contrast enhancement scan are executed sequentially as a single examination protocol (subtraction protocol). The user injects a contrast agent before the start of the pre-contrast enhancement scan. The scan controller 43 starts the pre-contrast enhancement scan in accordance with a manual instruction from the user via the input unit 47. After X-ray emission is performed a predetermined number of times for the pre-contrast enhancement scan, the scan controller 43 automatically stops the pre-contrast enhancement scan. Note that the contrast agent injector 60 may inject the contrast agent. That is, the scan controller 43 transmits an injection start signal to the contrast agent injector 60. Upon receiving the injection start signal, the contrast agent injector 60 automatically injects the contrast agent into the subject S. In synchronism with the transmission of the injection start signal to the contrast agent injector 60, the scan controller 43 transmits an emission start signal to the gantry controller 21. Alternatively, the contrast agent injector 60 may transmit an emission start signal to the scan controller 43 in synchronism with an injection operation to the contrast agent injector 60 by the user, and the scan controller 43 may transmit an emission start signal to the gantry controller 21 in response to the reception of the emission start signal. This can synchronize the injection of the contrast agent with X-ray emission in the monitoring scan. Upon the lapse of a predetermined waiting time after the stop of the pre-contrast enhancement scan, the scan controller 43 automatically starts the monitoring scan. This waiting time can be arbitrarily set. Note that the monitoring scan may start immediately after the stop of the pre-contrast enhancement scan without setting the waiting time. When the monitoring scan is performed and the contrast agent concentration (i.e., a statistical value based on the pixel values of a plurality of pixels in the monitoring region) reaches a threshold, the monitoring scan is stopped, and the post-contrast enhancement scan automatically starts upon the lapse of a predetermined period. After X-ray emission is performed a predetermined number of times for the post-contrast enhancement scan, the scan controller 43 automatically stops the post-contrast enhancement scan.

As described above, according to Example 2, the pre-contrast enhancement scan is automatically shifted to the monitoring scan. The labor of the subtraction protocol by the user is reduced, and the examination time is shortened, compared to Example 1.

After performing step SB6, the contrast enhancement examination according to the embodiment ends.

After the end of the contrast enhancement examination, the image processor 35 generates a subtraction image based on the pre-contrast enhancement CT image and the post-contrast enhancement CT image. The display unit 45 displays the subtraction image.

Figure 13:
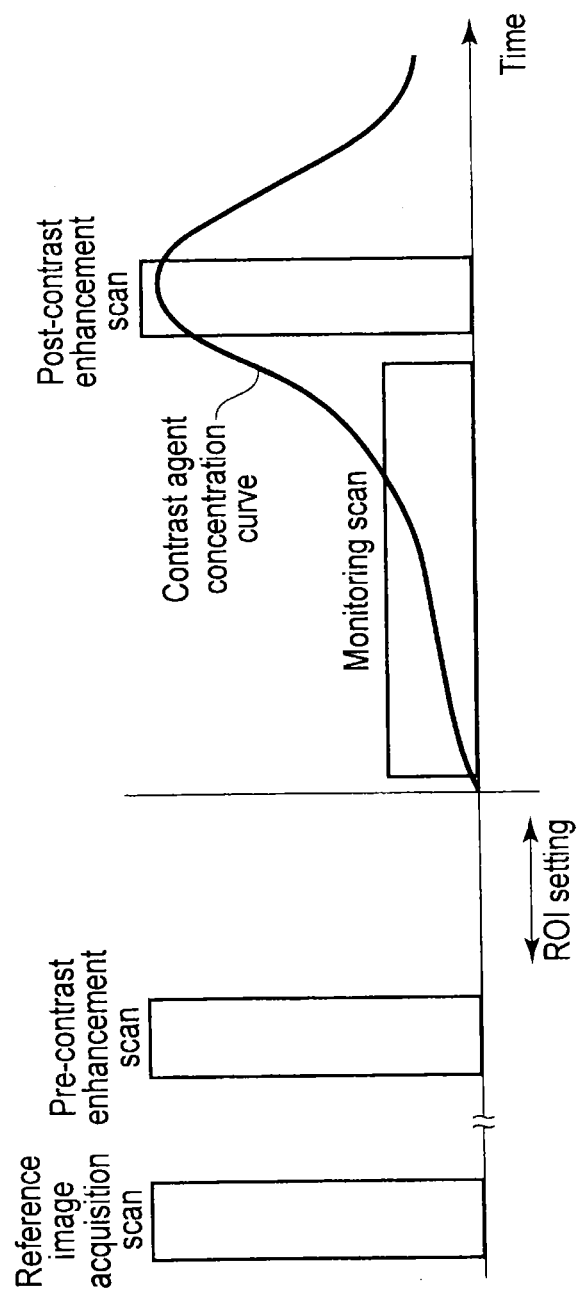
FIG. 13 is a graph schematically showing the sequence of the contrast enhancement examination in FIG. 12.

In the related art, the monitoring scan is a scan for the post-contrast enhancement scan. Hence, the monitoring scan and post-contrast enhancement scan are regarded as a set of examination protocols, and the two scans are performed without a break. However, the pre-contrast enhancement scan and the monitoring/post-contrast enhancement scan are regarded as completely individual scans. Thus, condition setting processing for the monitoring scan and post-contrast enhancement scan, and condition setting processing for the pre-contrast enhancement scan are performed individually, as shown in FIGS. 12 and 13. That is, as shown in FIGS. 12 and 13, condition setting processing and monitoring region setting processing for the monitoring scan and post-contrast enhancement scan are performed between the end of the pre-contrast enhancement scan and the start of the monitoring scan. A long time is therefore taken till the start of the monitoring scan after the end of the pre-contrast enhancement scan, and a subject may move during this period. In this case, the influence of the body motion or the like is imaged in addition to the influence of the contrast agent in a subtraction image between a pre-contrast enhancement CT image and a post-contrast enhancement CT image, impairing the image quality of the subtraction image.

The present inventors according to the embodiment have altered the role of the monitoring scan. That is, the present inventors according to the embodiment have positioned the monitoring scan as a scan which links the pre-contrast enhancement scan and post-contrast enhancement scan. As a result, a new efficient subtraction protocol for acquiring a subtraction image has been built.

The X-ray computed tomography imaging apparatus according to the embodiment implements optimization of the scan sequence of the subtraction protocol by building this new subtraction protocol. More specifically, the scan controller 43 executes the pre-contrast enhancement scan, monitoring scan, and post-contrast enhancement scan sequentially as a single examination protocol in accordance with preset imaging conditions and reconstruction conditions. In order to execute the pre-contrast enhancement scan, monitoring scan, and post-contrast enhancement scan sequentially as a single examination protocol, the imaging plan unit 37 performs condition setting processing at once for the pre-contrast enhancement scan, monitoring scan, and post-contrast enhancement scan at the preceding stage of the pre-contrast enhancement scan. Since neither condition setting processing nor monitoring region setting processing need be performed between the pre-contrast enhancement scan and the monitoring scan, the examination time from the start of the pre-contrast enhancement scan up to the end of the post-contrast enhancement scan is shortened. More specifically, processing from the start of the pre-contrast enhancement scan up to the end of the post-contrast enhancement scan can be completed in the time of one breath. This can minimize the body motion of the subject. That is, the embodiment can shorten the time of a shift from the pre-contrast enhancement scan to the monitoring scan, compared to the related art. In addition, the embodiment can minimize the influence of a difference such as the body motion of the subject, other than the contrast agent, in a subtraction image. With the synchronous setting function, the imaging plan unit 37 synchronously sets the same contents of the imaging conditions and reconstruction conditions of the pre-contrast enhancement scan, monitoring scan, and post-contrast enhancement scan. This can shorten the working time regarding condition setting processing of the pre-contrast enhancement scan, monitoring scan, and post-contrast enhancement scan.

Accordingly, the time of a shift from the pre-contrast enhancement scan to the monitoring scan can be shortened in the X-ray computed tomography imaging apparatus which executes three types of scans, i.e., the pre-contrast enhancement scan, monitoring scan, and post-contrast enhancement scan.

(Applications)

As described in the embodiment, a pre-contrast enhancement CT image and post-contrast enhancement CT image are generated by the subtraction protocol, and subtraction processing is performed on the pre-contrast enhancement CT image and post-contrast enhancement CT image to generate a subtraction image. In other words, the subtraction protocol is sometimes performed to obtain a subtraction image. In subtraction processing, there are various conditions (to be referred to as subtraction conditions hereinafter) in accordance with target portions. However, depending on the imaging conditions and reconstruction conditions of the subtraction protocol, the imaging conditions and reconstruction conditions may not match subtraction conditions for desired subtraction processing, and the subtraction processing may not be executed even by executing the subtraction protocol. In this case, it is necessary to set again the imaging conditions and reconstruction conditions of the subtraction protocol, and execute again the subtraction protocol. Re-execution of the subtraction protocol gives various disadvantages to both a medical staff and subject.

An X-ray computed tomography imaging apparatus according to an application of the embodiment determines, before execution of the subtraction protocol, whether subtraction processing can be executed. The X-ray computed tomography imaging apparatus according to the application will be explained. In the following description, the same reference numerals as those in the embodiment denote building components having almost the same functions, and a repetitive description thereof will be made, only as needed.

Figure 8:
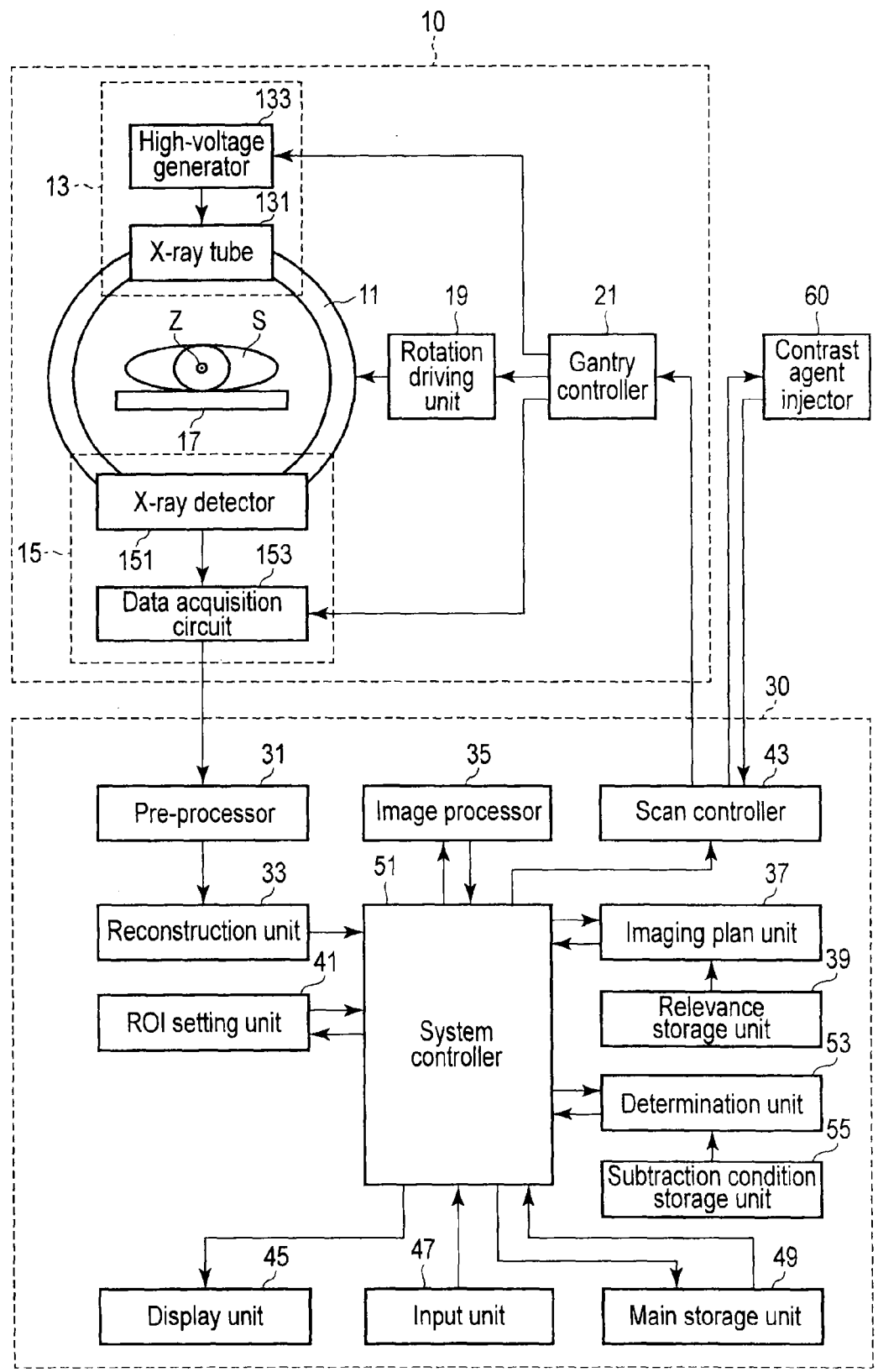
FIG. 8 is a view showing the arrangement of an X-ray computed tomography imaging apparatus according to an application of the embodiment.

FIG. 8 is a view showing the arrangement of the X-ray computed tomography imaging apparatus according to the application. As shown in FIG. 8, the X-ray computed tomography imaging apparatus according to the application further includes a determination unit 53 and subtraction condition storage unit 55.

Based on the item values of setting items for the imaging conditions and reconstruction conditions of the pre-contrast enhancement scan and post-contrast enhancement scan, and execution conditions for subtraction processing to be executed, the determination unit 53 determines whether subtraction processing can be executed. The execution conditions define allowable ranges when executing subtraction processing on the item values of setting items for the imaging conditions and reconstruction conditions of the pre-contrast enhancement scan and post-contrast enhancement scan. The execution conditions for subtraction processing will be called subtraction conditions. More specifically, the determination unit 53 executes determination processing in accordance with the subtraction conditions stored in the subtraction condition storage unit 55. Details of the determination processing will be described later.

For each of a plurality of types of subtraction processing, the subtraction condition storage unit 55 stores subtraction conditions for the subtraction processing. The subtraction conditions are defined by, e.g., an LUT or database. The subtraction conditions are assumed to be defined by an LUT, and this LUT will be called a subtraction condition table.

FIG. 9 is a table showing an example of the subtraction condition table. As shown in FIG. 9, types of subtraction processing are classified in accordance with, e.g., target portions in subtraction processing. For example, the target portions may be arbitrary portions of the human body and are, e.g., the heart, head, and lower limbs. The subtraction conditions are defined in the allowable ranges of the item values of the setting items of imaging conditions and reconstruction conditions set for the pre-contrast enhancement scan and post-contrast enhancement scan. Examples of the setting items are the enlargement ratio, reconstruction range, and overlapping range, as shown in FIG. 9. The enlargement ratio is defined by the magnification of the size of an image with respect to an actual size. The reconstruction range is defined by a length of the reconstruction range along the Z-axis. The overlapping range is defined as a length, along the Z-axis, of an overlapping range between a reconstruction range for the pre-contrast enhancement scan and a reconstruction range for the post-contrast enhancement scan. For example, in subtraction processing for ID 1, the target portion is the heart, the allowable range of the enlargement ratio is a range of 50 mm to 500 mm, and the allowable range of the reconstruction range is a range of smaller than 400 mm. Note that the user can arbitrarily change the values (allowable ranges) of the subtraction conditions via the input unit 47.

Figure 10:
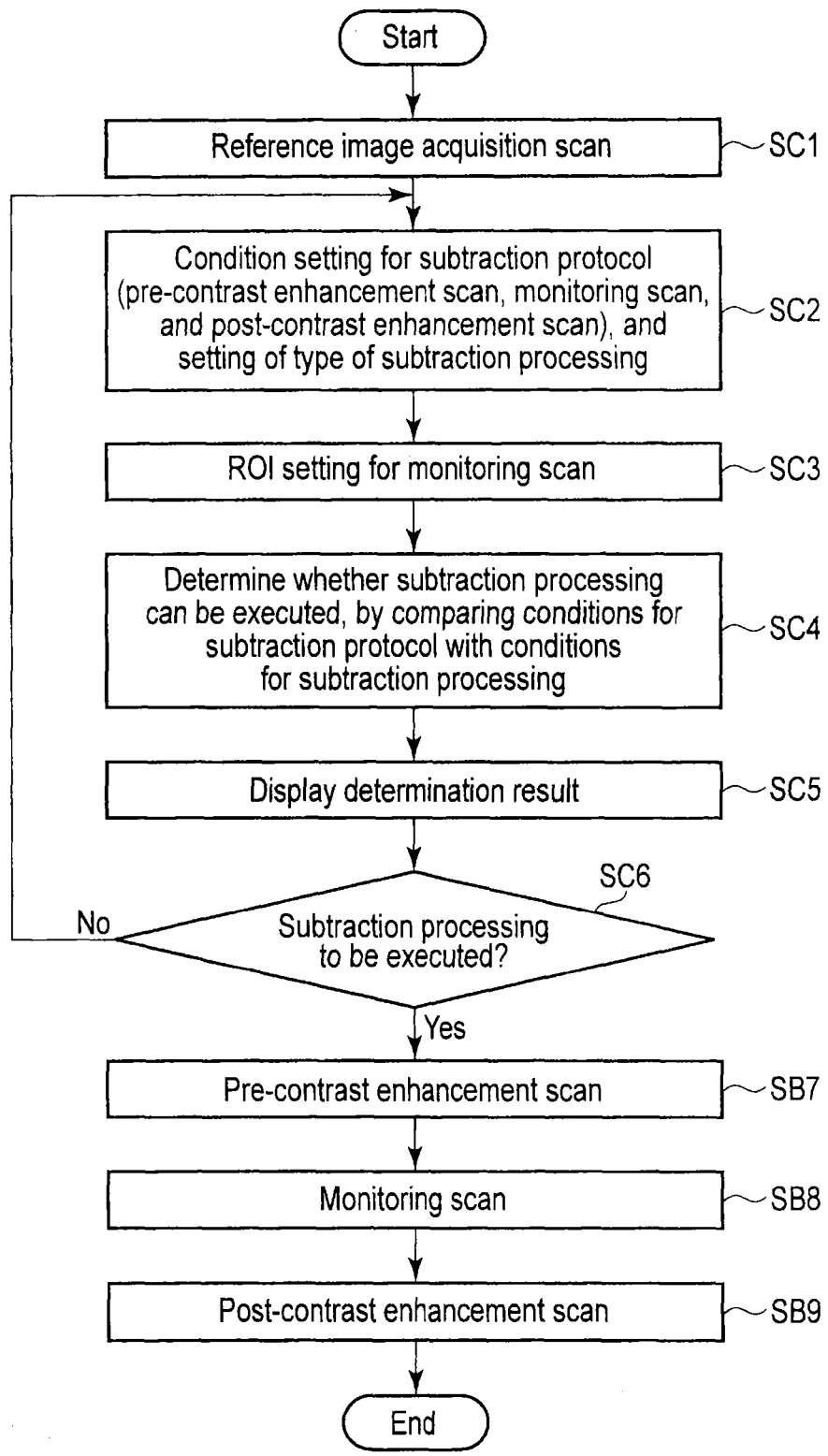
FIG. 10 is a flowchart showing the typical sequence of a contrast enhancement examination to be performed under the control of a system controller in FIG. 8.

Next, the flow of a contrast enhancement examination to be performed under the control of the system controller 51 according to the application will be explained. FIG. 10 is a flowchart showing the typical sequence of a contrast enhancement examination to be performed under the control of the system controller 51 according to the application.

As shown in FIG. 10, the reference image acquisition scan is performed first (step SC1). The reference image acquisition scan in step SC1 is almost the same as the reference image acquisition scan in step SB1 of FIG. 5, and a description thereof will not be repeated.

After performing step SC1, the imaging plan of the subtraction protocol is determined (step SC2). In step SC2, the imaging plan unit 37 determines the imaging plan of the subtraction protocol by the above-described imaging plan processing. Also, the imaging plan unit 37 determines the type of subtraction processing in accordance with an instruction from the user via the input unit 47. For example, when performing subtraction processing for the lower limbs, the user designates the lower limbs as the type of subtraction processing. Typically, the type of subtraction processing coincides with the imaging target portion of the subtraction protocol.

After performing step SC2, the ROI setting unit 41 performs ROI setting processing (step SC3). ROI setting processing in step SC3 is almost the same as ROI setting processing in step SB3 of FIG. 5, and a description thereof will not be repeated.

After performing step SC3, the determination unit 53 performs determination processing (step SC4). In step SC4, the determination unit 53 determines whether subtraction processing can be executed, by comparing the item values of setting items for the imaging conditions and reconstruction conditions of the pre-contrast enhancement scan and post-contrast enhancement scan set in step SC2, with the subtraction conditions (allowable ranges) for subtraction processing of the type designated in step SC2. More specifically, if the item value of a setting item falls in the allowable range, the determination unit 53 determines that subtraction processing can be executed. If the item value of a setting item falls outside the allowable range, the determination unit 53 determines that subtraction processing cannot be executed. For example, based on the item value of a setting item designated by the user among a plurality of setting items, the determination unit 53 determines whether subtraction processing can be executed. The type of setting item can be arbitrarily set via the input unit 47.

FIG. 11 is a table for explaining determination processing by the determination unit 53. In FIG. 11, the type of subtraction processing is the heart shown in FIG. 9, and the enlargement ratio shown in FIG. 9 is exemplified as a setting item to be compared. That is, the subtraction condition (allowable range) is the range of 50 mm to 500 mm. Assume that the enlargement ratio of a given subtraction protocol (ID 1) is 600 mm, and the enlargement ratio of another subtraction protocol (ID 2) is 400 mm. The determination unit 53 determines whether the enlargement ratio "600 mm" for the subtraction protocol of ID 1 falls within the allowable range of the enlargement ratio. In this case, the enlargement ratio "600 mm" for the subtraction protocol falls outside the allowable range "range of 50 mm to 500 mm", and the determination unit 53 determines that subtraction processing cannot be executed. Similarly, the determination unit 53 determines whether the enlargement ratio "400 mm" for the subtraction protocol of ID 2 falls within the allowable range of the enlargement ratio. In this case, the enlargement ratio "400 mm" for the subtraction protocol of ID 2 falls within the allowable range "range of 50 mm to 500 mm", and the determination unit 53 determines that subtraction processing can be executed.

Note that the above-described processing contents are merely an example of determination processing, and determination processing according to the embodiment is not limited to only the above-described processing contents. For example, the determination unit 53 may compare the item value of each of a plurality of setting items with the allowable range, and if the item value of any one of the plurality of setting items falls outside the allowable range, may determine that subtraction processing cannot be executed. Alternatively, only when the item value of any one preferential setting item among a plurality of setting items falls within the allowable range, the item value of another setting item may be compared with the allowable range. For example, when the overlapping range is narrow by a predetermined value or more, subtraction processing cannot be performed. Therefore, the overlapping range is preferably set as a preferential setting item. In this case, the determination unit 53 preferably first determines whether the item value of the overlapping range falls within the allowable range, and only if the item value of the overlapping range falls within the allowable range, compares the item value of another setting item such as the enlargement ratio with the allowable range. This can increase the processing efficiency while maintaining the accuracy of determination processing. Alternatively, if the item value of any one of a plurality of setting items falls within the allowable range, the determination unit 53 may determine that subtraction processing can be executed. This can further increase the processing efficiency of determination processing.

After performing step SC4, the display unit 45 determines the determination result of determination processing in step SC4 (step SC5). In step SC5, the display unit 45 displays a message corresponding to the determination result. If it is determined that subtraction processing can be executed, the display unit 45 displays a message such as "imaging conditions and reconstruction conditions are suited to subtraction processing". If it is determined that subtraction processing cannot be executed, the display unit 45 displays a message such as "imaging conditions and reconstruction conditions are not suited to subtraction processing".

After performing step SC5, the system controller 51 waits for an instruction from the user via the input unit 47 that represents whether to execute subtraction processing (step SC6). For example, in step SC5, the display unit 45 preferably displays an imaging button and condition re-setting button together with a message corresponding to the determination result. The user confirms the determination result, and if he determines to set conditions again, presses the condition re-setting button via the input unit 47. If the condition re-setting button has been pressed (step SC6: NO), the system controller 51 returns to step SC2 to repeat again steps SC2 to SC6.

If it is determined to start imaging under the conditions set in step SC2, the user presses the imaging button via the input unit 47. If the imaging button has been pressed (step SC6: YES), the scan controller 43 controls the X-ray generation unit 13 and X-ray detection unit 15 to execute the pre-contrast enhancement scan, monitoring scan, post-contrast enhancement scan sequentially as a single examination protocol.

More specifically, first, the pre-contrast enhancement scan targeting the imaging portion of the subject S is performed (step SC7). Based on projection data acquired by the pre-contrast enhancement scan, the reconstruction unit 33 generates a pre-contrast enhancement CT image in accordance with reconstruction conditions for the pre-contrast enhancement scan. The pre-contrast enhancement scan in step SC7 is almost the same as the pre-contrast enhancement scan in step SB4 of FIG. 5, and a description thereof will not be repeated.

After performing step SC7, the scan controller 43 executes the monitoring scan targeting a monitoring region set in step SC3 (step SC8). The monitoring scan in step SC8 is almost the same as the monitoring scan in step SB5 of FIG. 5, and a description thereof will not be repeated.

After performing step SC8, the scan controller 43 executes the post-contrast enhancement scan targeting the imaging portion of the subject S (step SC9). Based on projection data acquired by the post-contrast enhancement scan, the reconstruction unit 33 generates a post-contrast enhancement CT image in accordance with the reconstruction conditions for the post-contrast enhancement scan. The post-contrast enhancement scan in step SC9 is almost the same as the post-contrast enhancement scan in step SB6 of FIG. 5, and a description thereof will not be repeated.

After performing step SC9, the contrast enhancement examination according to the application ends.

After the end of the contrast enhancement examination, the image processor 35 automatically generates a subtraction image based on the pre-contrast enhancement CT image and the post-contrast enhancement CT image. The display unit 45 displays the generated subtraction image.

As described above, before executing the subtraction protocol, an X-ray computed tomography imaging apparatus according to the application can determine whether the imaging conditions and reconstruction conditions of the subtraction protocol match the subtraction conditions of subtraction processing to be executed. Re-execution of the subtraction protocol owing to a mismatch of the imaging conditions and reconstruction conditions can be prevented. This increases the efficiency of the contrast enhancement examination.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. An X-ray computed tomography imaging apparatus comprising:
   an X-ray generation unit configured to generate X-rays;
   an X-ray detection unit configured to detect X-rays which have been generated from the X-ray generation unit and have passed through a subject;
   an imaging condition setting unit configured to set imaging conditions for a pre-contrast enhancement scan, a monitoring scan, and a post-contrast enhancement scan;
   a region-of-interest setting unit configured to set a region of interest for the monitoring scan in a reference image generated by a reference image scan executed before the pre-contrast enhancement scan, the monitoring scan, and the post-contrast enhancement scan; and
   a scan control unit configured to control the X-ray generation unit and the X-ray detection unit based on the imaging conditions to sequentially execute the pre-contrast enhancement scan, the monitoring scan, and the post-contrast enhancement scan.

2. The apparatus according to claim 1, further comprising:
   a relevance storage unit configured to store relevance, between scan types, of a plurality of setting items included in imaging conditions and reconstruction conditions of the pre-contrast enhancement scan, the monitoring scan, and the post-contrast enhancement scan; and
   an input unit configured to accept a user instruction for setting imaging conditions and reconstruction conditions for a scan type to be set among the pre-contrast enhancement scan, the monitoring scan, and the post-contrast enhancement scan,
   wherein the imaging condition setting unit sets, based on the relevance between the scan types in synchronism with an instruction from a user via the input unit, item values of a plurality of setting items included in imaging conditions and reconstruction conditions of scan types other than the scan type to be set.

3. The apparatus according to claim 2, wherein when an item value of a setting item of a specific type in the scan type to be set is input via the input unit, the imaging condition setting unit inputs the input item value to the setting item of the specific type in the scan types other than the scan type to be set.

4. The apparatus according to claim 2, wherein when an item value of a setting item of a specific type in the scan type to be set is input via the input unit, the imaging condition setting unit restricts input of an item value to the setting item of the specific type in the scan types other than the scan type to be set.

5. The apparatus according to claim 2, wherein the imaging condition setting unit registers, as a set of scan types, a combination of a plurality of scan types selected in accordance with an instruction from the user via the input unit.

6. The apparatus according to claim 2, wherein the scan control unit starts the pre-contrast enhancement scan upon receiving a start instruction from a user via the input unit, and executes the monitoring scan and the post-contrast enhancement scan upon receiving a start instruction from the user via the input unit after an end of the pre-contrast enhancement scan.

7. The apparatus according to claim 2, wherein the scan control unit automatically executes the pre-contrast enhancement scan, the monitoring scan, and the post-contrast enhancement scan sequentially upon receiving a start instruction from the input unit.

8. The apparatus according to claim 1, further comprising:
a reconstruction unit configured to generate a pre-contrast enhancement CT image based on an output from the X-ray detection unit in the pre-contrast enhancement scan, and generate a post-contrast enhancement CT image based on an output from the X-ray detection unit in the post-contrast enhancement scan; and
an image processing unit configured to generate a subtraction image based on the pre-contrast enhancement CT image and the post-contrast enhancement CT image.

9. The apparatus according to claim 8, further comprising a display unit configured to display the subtraction image.

10. The apparatus according to claim 1, further comprising:
a determination unit configured to determine, based on item values of setting items for imaging conditions and reconstruction conditions of the pre-contrast enhancement scan and post-contrast enhancement scan, and execution conditions for subtraction processing to be executed, whether the subtraction processing to be executed can be executed; and
a display unit configured to display a result of determination by the determination unit.

11. The apparatus according to claim 10, further comprising a subtraction condition storage unit configured to store execution conditions for each of a plurality of types of subtraction processing,
wherein the determination unit determines, based on the item values of the setting items for the imaging conditions and reconstruction conditions of the pre-contrast enhancement scan and post-contrast enhancement scan, and the execution conditions for the subtraction processing to be executed out of the plurality of types of subtraction processing, whether the subtraction processing to be executed can be executed.

12. The apparatus according to claim 10, wherein the execution conditions define allowable ranges of the item values of the setting items for the imaging conditions and reconstruction conditions of the pre-contrast enhancement scan and post-contrast enhancement scan.

13. The apparatus according to claim 10, further comprising a reconstruction unit and an image processing unit,
wherein when an execution of the subtraction processing to be executed is designates after the display unit displays the determination result, the scan control unit controls the X-ray generation unit and the X-ray detection unit to sequentially execute the pre-contrast enhancement scan, the monitoring scan, and the post-contrast enhancement scan,
the reconstruction unit generates a pre-contrast enhancement CT image based on an output from the X-ray detection unit in the pre-contrast enhancement scan, and generates a post-contrast enhancement CT image based on an output from the X-ray detection unit in the post-contrast enhancement scan, and
the image processing unit generates a subtraction image based on the pre-contrast enhancement CT image and the post-contrast enhancement CT image.

* * * * *